United States Patent
Erf

(10) Patent No.: US 8,216,551 B2
(45) Date of Patent: Jul. 10, 2012

(54) IN VIVO SYSTEM TO MONITOR TISSUE RESPONSES IN BIRDS

(75) Inventor: Gisela F. Erf, Fayetteville, AR (US)

(73) Assignee: The Board of Trustees of the University of Arkansas, Little Rock, AR (US)

(*) Notice: Subject to any disclaimer, the term of this patent is extended or adjusted under 35 U.S.C. 154(b) by 423 days.

(21) Appl. No.: 12/467,727

(22) Filed: May 18, 2009

(65) Prior Publication Data

US 2009/0285758 A1    Nov. 19, 2009

Related U.S. Application Data

(60) Provisional application No. 61/053,996, filed on May 16, 2008.

(51) Int. Cl.
*A61K 49/00* (2006.01)
(52) U.S. Cl. .................................... 424/9.2; 435/349
(58) Field of Classification Search .................. None
See application file for complete search history.

(56) References Cited

OTHER PUBLICATIONS

Blondeau (Vet. Res. (Mar. 2007), vol. 38,pp. 419-433).*
Abdul-Careen, M.F., B.D. Hunter, A.J. Sarson, P. Parvizi, H.R. Haghighi, L. Read, M. Heidari, and S. Sharif, 2008. Host responses are induced in feathers of chickens infected with Marek's disease virus, Virology 370.323-332.
Nair M. Krishnan. 1973. The early inflammatory reaction in fowl. Acta Vet. Scand. Suppl. 42:1-13.
Erf, G.F., A.V. Trejo-Skalli, and J.R. Smyth, Jr, 1995. T cells in regenerating feathers of Smyth line chickens with vitiligo. Clin. Immunol. Immunopathol. 76:120-126.
Wang, X., and G.F. Erf, 2004, Apoptosis in feathers of Smyth line chickens with autoimmune vitiligo. J. Autoimmun. 22: 21-30.
Shresta, S., J.R. Smyth, Jr., and G.F. Erf, 1997, Profiles of pulp infilrating lymphocytes at various times throughout feather regeneration in Smyth line chickens with vitiligo. Autoimmunity 25: 193-201.
Wang, X., and G.F. Erf, 2003. Melanocyte-specific cell mediated immune response in vitiliginous Smyth line chickens J. Autoimmun. 21: 149-160.
Wijesekera, H. D., and G.F. Erf, 2004. Antioxidant capacity and oxidative stress in vitiliginous Smyth line chickens and controls. Pigment Cell Res. 17:440.
Lockhart, B. R., and G.F. Erf, 2004. Oxidative stress and antioxidant levels in feather-derived and embryo-derived melanocytes from vitiligo-prone Smyth line and normally pigmented chickens. Pigment Cells Res. 14:440.
Plumlee, B.L ., X. Wang, and G.F. Erf, 2006, Interferon-gamma expression in feathers from vitiliginous Smyth line chickens. J. Immunology 176:S283.
Plumlee, B.L., and G.F. Erf, 2006. Differential cytokine expression in feathers from vitiliginous Smyth line chickens. Pigment Cell Res. 19:371.
Erf, G.F., B.L. Plumlee, K.D. Bateman, C.T. Trovillion, and R.C. Finley, 2007. Examination of early events in the development of autoimmune vitiligo in the Smyth line chicken model. Pigment Cell Res. 20:329.
Erf, G.F., B. Lockhart, K. Bateman, R. Finley, and O.T. Bowen. The feather as an in vivo test tube for tissue immune responses. Poult. Sci. 86 (Suppl. 1):143. (Oral presentaion at the annual meeting of the Poultry Science Association, Jul. 2007).
Erf, G.F., B. Lockhart, O.T. Bowen, K. Bateman, and R. Finley. 2007. Using the chicken feathers as a window into cell-mediated tissue responses. J. Immunol. 178:99.12. (presented in May 2007 as a poster at an annual meeting of the American Association of Immunologists).
Higgins, S.E., S.L. Layton, A.D. Wolfenden, K. Cole, B.M. Hargis, and G.F. Erf. 2007. In vivo characterization of the recall response to antigen in chickens vaccinated with attenuated *Salmonella* mutants expressing M2e protein. Poult. Sci. 86 (Suppl. 1):53, (poster presentation at the annual meeting of Poultry Science Association, Jul. 2007).

* cited by examiner

*Primary Examiner* — Susan Hoffman
(74) *Attorney, Agent, or Firm* — Andrus, Sceales, Starke & Sawall, LLP

(57) ABSTRACT

Methods of evaluating the tissue response to an agent in birds are provided. Also disclosed are methods of monitoring exposure to agents in birds and methods of determining the efficacy of vaccines.

20 Claims, 4 Drawing Sheets

IN VIVO SYSTEM TO MONITOR TISSUE RESPONSES IN BIRDS

CROSS-REFERENCE TO RELATED APPLICATIONS

This application claims the benefit of U.S. Provisional Application No. 61/053,996 filed May 16, 2008, the content of which is incorporated herein by reference in its entirety.

STATEMENT REGARDING FEDERALLY SPONSORED RESEARCH

This invention was made with government support under grant number 2008-36100-06005, awarded by the USDA/CSREES. The government has certain rights in the invention.

BACKGROUND

Fundamental knowledge regarding events leading to effective immune response and memory development in poultry is lacking. This is particularly true for cellular responses and tissue responses in general. To study and monitor immune responses in an individual, non-terminal, minimally invasive procedures are essential. Peripheral blood and tissue secretions have served as an excellent window for humoral immune activities. Peripheral blood leukocytes can be used for various down-stream analyses. Blood plasma can be analyzed for antibodies and various soluble factors related to innate and adaptive immune response activities. However, because blood serves as a vehicle for leukocytes to travel to tissues containing the target antigen, this approach is limited, particularly regarding cellular/tissue activities. Thus, activated leukocytes or antigen-specific clones of lymphocytes represent only a minor portion of circulating cells. Hence to gain insight into innate and adaptive cellular immune activities and host/pathogen/immune interactions, in situ immune response activities will need to be examined.

SUMMARY OF THE INVENTION

Methods of evaluating a tissue response to an agent in birds are provided herein. The method includes administering the agent to a bird, injecting the agent or a portion thereof into a first feather tip of the bird at a time after the agent was first administered to the bird and then evaluating the tissue response to the agent in the first feather tip.

In another aspect, methods of monitoring exposure of a bird to an agent are provided. These methods include injecting a first feather tip of a bird with the agent and then monitoring the tissue response to the agent in the first feather tip. The development of a tissue response in the first feather tip is indicative of exposure of the bird to the agent.

In yet another aspect, methods of evaluating a tissue response of a bird to an agent are provided. These methods include administering the agent to the bird and then evaluating the tissue response to the agent in a first feather tip.

In still another aspect, methods of evaluating the effect of agents on the tissue response of a bird are provided. These methods include administering the agent to the bird and then injecting an antigen into a first feather tip of the bird. The tissue response to the antigen is then evaluated.

BRIEF DESCRIPTION OF THE DRAWINGS

FIG. 3A shows H/E staining of PBS-injected feathers. FIGS. 3B-D show Mb-injected feathers 4, 24 and 48 hours post-injection, respectively. FIGS. 3E-F show immunohistochemical staining using an isotype control monoclonal antibody or a CD4 monoclonal antibody after injection, respectively.

FIG. 3G-K is a set of graphs showing the change over time in the percentage of the pulp area occupied by each of the indicated cell types.

DETAILED DESCRIPTION

A minimally invasive bioassay system for monitoring and evaluating cellular and tissue responses, particularly immune responses in vivo is described herein. Specifically, the growing feather of birds was identified as a suitable integumentary tissue that allows for tissue responses to be examined after administration of agents to birds. The growing feather of birds is called the feather tip and refers to the newest portion of a growing feather. The feather tip is the approximately 0.5-1 cm portion of the feather closest to the bird. This is the portion of the feather undergoing active growth. The feather tip can be seen in FIG. 1.

The methods provided herein allow evaluation of tissue responses in birds by administering an agent to the bird, either locally or systemically, and then evaluating the tissue response to the agent in a feather tip. Alternatively, methods are also provided in which the agent is administered to a bird and then a feather tip of the bird is injected with the agent or a portion thereof. The subsequent tissue response to the agent can be evaluated in the feather tip. "Administering an agent" is intended to encompass both intentional administration of the agent and environmental exposure to the agent. The methods may be useful to studying the innate or cellular immune responses to the agent and the inflammatory responses to the agent.

Growing feathers are found on all young feathered birds. Those of skill in the art will appreciate that the methods described herein could be used with any feathered bird including but not limited to members of the poultry species such as turkeys and chickens. Other birds useful in the methods described herein include, but are not limited to, quail, emu, bluejay, crow, ducks, geese, or any other bird with growing feathers. In chickens, growing feathers are present in birds between 2 and 22 weeks of age (depending on the type of chicken). Those of skill in the art will appreciate that different birds will have growing feathers available for differing periods of time during their life and that plucking stimulates regrowth of feathers (feather regeneration).

As shown in FIG. 1, the feather tip can be injected with agents such as antigens as described in the Examples. Chicken feather tips are about 1 cm in length so in the Examples a microinjection system is utilized to inject about 10 μl of the agent in a vehicle into the pulp of the feather. Injection of the feather tip does not result in bleeding or damage to the growing feather and there is no indication of pain from the bird during injection. This feature is clearly distinct from the use of other integumentary tissues such as the wing web or wattle which are quite sensitive tissues.

Agents suitable for use in the methods include but are not limited to polypeptides, polynucleotides, carbohydrates, lipids, nanoparticles, microbes, chemicals such as pharmaceuticals or candidate pharmaceuticals, cells and portions or fragments thereof. Specifically, agents include, but are not limited to antigens, adjuvants, immunomodulators, vaccines, microorganisms, syngeneic cells, allogeneic cells, xenogeneic cells, and other soluble factors produced during an inflammatory or other immune response. Pharmaceuticals include any chemical composition that has an effect on a system or cell in an animal. The agents may be solubilzed in any vehicle compatible for in vivo administration, such as phosphate buffered saline (PBS).

Figure 1:
FIG. 1 is a set of photographs depicting the feather tip and a cartoon depicting microinjection of the feather tip.

As discussed above, the agent may be administered by direct injection into the feather tip, or may be administered by any other suitable means. For example, the agent may be administered systemically by intraperitoneal, intravascular, intramuscular or skin (epidermal, transdermal etc.) injection. The agent may also be administered by adding the vehicle to the bird's feed or drink so that it is ingested. The agent may also be administered by aerosolization and inhalation. Alternatively, the agent may be administered naturally through environmental exposure.

For analysis of the tissue response to an agent, the feather can be removed from the bird by any means known to those of skill in the art. Pulling of the feather may be achieved by holding the skin surrounding the feather and quickly pulling on a cut portion (top) of the feather with forceps. Collected feathers can then be trimmed leaving only the newest growth or the feather tip intact (See FIG. 1). The feather tips can then be processed in a variety of ways, as described in detail below, in order to assess the tissue response to the agent. Multiple feathers may be harvested from the same bird over time and harvesting of feathers provides a minimally invasive means to monitor and evaluate the tissue responses occurring in vivo.

Prior methods of measuring tissue responses in birds required that the birds be euthanized or limited the types of assays that could be done to monitor the responses. Using the methods described herein the tissue response to an agent can be measured over time in the same animal. One means of measuring the response over time would be to administer an agent to the bird and then inject multiple feather tips substantially simultaneously with the agent or a portion thereof. The feather tips can then be harvested at different times after injection to monitor and produce a time course of the developing tissue response to the agent. Alternatively, an agent could be administered to a bird and then multiple feather tips could be injected at different times and the feather harvested at a defined time after the injection to allow one to monitor the change in the recall tissue response over time.

It is envisioned that the method of the invention could be used to evaluate the immune response to vaccination. For example, the bird could be administered the vaccine and then the immune response to the vaccine could be monitored by injecting a feather tip with at least a portion of the vaccine. The feather could be harvested and the vaccine specific immune response assayed. The development of a tissue response in the feather tip may be indicative of a vaccine specific immune response. Thus, the method may be used to monitor or assay the effectiveness of vaccination.

Also provided are methods of monitoring exposure to an agent. These methods include injecting a first feather tip of the bird with an agent and then monitoring the tissue response to the agent in the first feather tip. The development of the tissue response may be indicative of exposure to the agent. For example, a sentinel animal in a flock could be injected with an agent in a feather tip and the tissue response to the agent monitored. The development of a tissue response in the feather tip may be indicative of exposure to the agent. This could be used to monitor the exposure of a flock of birds to a particular agent and may provide information on the spread of disease or the health of a flock. Significantly, the same sentinel animal could be monitored over time, or different animals could be monitored.

The types of tissue responses that can be evaluated or monitored include but are not limited to innate immune responses, adaptive immune responses, inflammatory responses, cell mediated immune responses, and humoral immune responses as well as vascular, local tissue cellular and neuronal responses. The feather tips can be evaluated in a variety of ways including, but not limited to, histological analysis or immunohistochemistry of the feather tip and the cells infiltrating the feather tip, harvesting cells from the feather tip for downstream assays or in vitro culture, assessing nucleic acid expression or polypeptide expression, and assessing enzyme activity. Those of skill in the art will appreciate the variety of ways in which the feather tips and the cells therein could be analyzed, including but not limited to FACS analysis, PCR, RT-PCR (including real-time PCR), Western blots, Northern blots, in vitro proliferation assays, assessment of oxidative radical production and antioxidant levels by enzymatic assays, and assessment of oxidative damage in the cells.

Methods of evaluating the effect of agents on the tissue response of birds are also provided. In these methods, an agent is administered to the bird and an antigen is injected into a first feather tip of the bird. The tissue response to the antigen is evaluated after exposure to the antigen and may be compared to a control. Those of skill in the art will appreciate a variety of suitable controls could be used for the purposes of comparison. For example, the response in the first feather could be compared to the response in a feather from the same bird that is injected with vehicle alone or not injected at all. Alternatively, the response in the first feather may be compared to the response to the antigen in a feather after injection into a feather tip in a bird that was not administered the agent.

In addition in the methods described above, the agent may be injected into a second feather tip of the bird. The second feather may be harvested from the bird. The first feather and second feather tip may be injected at substantially the same time or at different times. The first feather and the second feather may also be harvested at substantially the same time or at different times to evaluate the tissue responses.

The Examples below provide evidence that the feather tip can be used as an integumentary tissue to monitor tissue responses in birds. In Example 1, feather tips and wing webs were injected with LPS or PHA and tissues were harvested to monitor the development of leukocyte infiltration in response. The results presented demonstrate that the feather tip produces similar results as the wing web but provides a less invasive means of monitoring tissue responses. Example 2 and 3 demonstrate that the feather tip is also an appropriate tissue for measuring the recall response to agents.

From these preliminary studies, several advantages of using the feather compared to other integumentary tissues such as the wing web and wattle have become clear. First, the feather provides a defined area (unit) of tissue response activity compared to the wider distribution of antigen and tissue response activities in the wattle or wing web tissue. Second, injection of the feather appears to be painless or causes little discomfort to the bird, especially as compared to methods involving the sensitive wattle. Third, the feather tissue is easier to process than skin and wing web. Fourth, it is possible to measure the recall response to several antigens simultaneously by injecting several feathers of the same bird with different antigens or agents. Fifth, collection of feather tissue was minimally invasive (similar to or less invasive than taking a blood sample), whereas the birds were euthanized to collect wing webs or wattles. These advantages, together with the similarities in leukocyte profiles post-LPS and -PHA injection demonstrated in Example 1 and the recall response to M.b. between the three integumentary tissues examined in Example 2, strongly support the use of the growing feather as a window and "in vivo test-tube" into cellular immune activities.

EXAMPLES

Materials and Methods

Feather injection: For injection of growing feathers, the emerging barbs of selected feathers were trimmed with scissors to 1-2 mm above the sheath of the growing feather. The sheath and skin surrounding the bottom of the growing feather was marked with green permanent marker. The prepared feathers were injected with 10 µL of the indicated treatments using a Hamilton 50 µL microsyringe and 31×0.5 syringe needles. The needle was inserted in the center of the feather, whereby the length of the needle enters the pulp no more than two-thirds of the length of the sheath-covered feather and the treatment is deposited in the center of the pulp (FIG. 1). Using this approach, the natural protection of the pulp from external exposure provided by the epidermis and the keratinized barbs at the top portion of the sheath remains in place. At the indicated times post-injection, feathers were plucked with forceps applied to the very top of the feather while holding the skin with the other hand.

Paraffin Sections: Paraffin tissue sections were prepared and stained in the Histology Service Laboratory located in the Center for Poultry Science. To optimize the ability to identify various types of leukocytes and tissues, several stains were used, including the May-Grünwald Giemsa stain (leukocyte identification), Hematoxylin/Eosin stain (general architecture). A 10 mm ocular grid was used to quantify cells/virus in the pulp and data expressed as # of cells/mm$^2$ (Erf, G. F., A. V. Trejo-Skalli, and J. R. Smyth, Jr. 1995. T cells in regenerating feathers of Smyth line chickens with vitiligo. Clin. Immunol. Immunopathol. 76:120-126 and Erf, G. F., A. V. Trejo-Skalli, M. Poulin, and J. R. Smyth, Jr. 1997. Dermal lymphoid aggregates in autoimmune Smyth line chickens. Vet. Immun. Immunopathol. 58:335-343.).

Immunohistochemistry and Image Analysis: Frozen tissue sections (7 µm) were prepared using a Micron cryostat and stained using a panel of commercially available mouse anti-chicken monoclonal antibodies and an indirect immunoperoxidase staining procedure described by Erf and colleagues (See Erf, G. F., A. V. Trejo-Skalli, and J. R. Smyth, Jr. 1995. T cells in regenerating feathers of Smyth line chickens with vitiligo. Clin. Immunol. Immunopathol. 76:120-126; Erf, G. F., A. V. Trejo-Skalli, M. Poulin, and J. R. Smyth, Jr. 1997. Dermal lymphoid aggregates in autoimmune Smyth line chickens. Vet. Immun. Immunopathol. 58:335-343 and Wang X., and G. F. Erf. 2004. Apoptosis in feathers of Smyth line chickens with autoimmune vitiligo. J. Autoimmun. 22: 21-30.). Stained sections were counter stained with Methyl Green stain. Cells/cell surface markers to be identified may include: chicken monocyte/macrophages (KUL01 antibody), T cell subsets (CD4, CD8, γδ TCR, αβ TCR), B cells (Bu-1, IgG, IgM), thrombocytes (11C3—Serotec, Raleigh, N.C.), MCAM (cellular adhesion molecule expressed on capillary endothelial cells), MHC class II (Ia; in chickens expressed on antigen-presenting cells, B cells, activated T cells and endothelial cells), MHC class I, CD44 (adhesion molecule expressed on effector/memory cells), CD14, TLR4 (LPS receptor components) and TLR 2 (PG receptor) (Tularik, South San Francisco, Calif.).[85] Unless otherwise indicated, monoclonal antibodies were obtained from Southern Biotechnology Associates, Inc. Tissue sections were microscopically examined for location of the infiltrates and general distribution of the various cell types/markers within the pulp. The area occupied by stained cells was quantified by image analysis using Image-Pro Software and expressed as percent of total area examined. Depending on the Example and indices obtained from conventional histology, frozen sections were stained with a focused panel of the markers listed above.

Example 1

Figure 2:
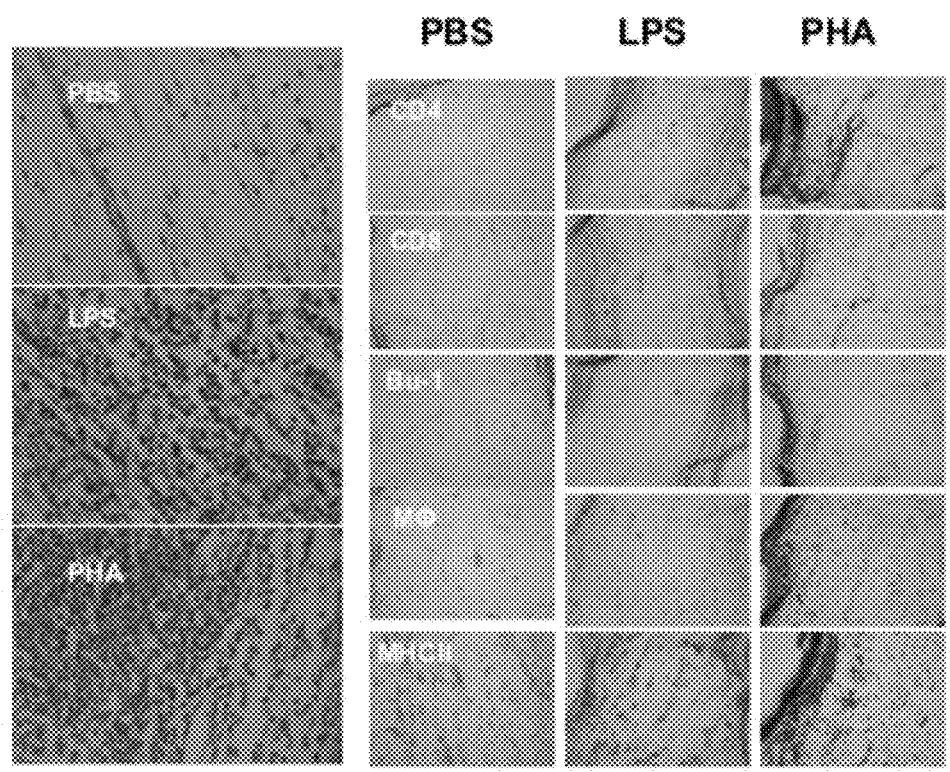
FIG. 2 is a set of photomicrographs showing the immune cell infiltration into the pulp of feathers 6 hours after lipopolysaccharide (LPS) or phytohaemagglutinin (PHA) injection after H/E staining or immunohistochemistry for the indicated markers.

Examination of the In Situ Response to Lipopolysaccharide (LPS, Inflammatory Mediator) or PHA To examine the local tissue response initiated by LPS and PHA in feathers and wing-webs (a more conventional integumentary tissue for immune response studies), the left and right wing webs and feathers (three on each breast tract) of 12-wk-old egg-type roosters were injected with 100 µL and 10 µL, respectively, of LPS (1 mg/mL), PHA (mg/mL) or PBS (vehicle) (FIG. 1). Six hours later, the birds (8 per treatment) were euthanized and tissues collected. Tissue from the left side of the bird was used for histology and those from the right side for immunohistochemistry. Microscopic examination revealed that PBS injection was not associated with leukocyte infiltration in the feather pulp. However, both injection of LPS and PHA resulted in extensive leukocyte infiltration by 6 hours. Nearly identical observations were made in the wing webs and feathers (FIG. 2—feather). The infiltrate consisted primarily of heterophils (the avian counterpart to neutrophils) in LPS injected-tissues, whereas for PHA injection, the infiltrate consisted of heterophils and mononuclear cells (FIG. 2). Leukocytes entered the tissues by adherence to venules. Six hours post-LPS injection, the leukocyte infiltrate appeared to contain no lymphocytes and only few monocytes/macrophages. However, there was a noticeable increase in MHC class II expression, suggesting the presence of interferon-γ. Six-hours post PHA-injection, mononuclear cells in the infiltrate included primarily CD4+ cells, which tended to form aggregates, few evenly distributed CD8+ cells and a number of macrophages/monocytes. MHC class II expression in the tissues was substantially increased, and coincided with areas of CD4+ cell aggregates and vascular tissue, suggesting that CD4+ T cells were activated and that IFN-γ was present in this inflammatory tissue (Erf, G. F., B. Lockhart, O. T. Bowen, K. Bateman, and R. Finley. 2007. Using the chicken feather as a window into cell-mediated tissue responses. J. Immunol. 178: 99.12.). These studies support the use of the feather for examination of in situ immune activities.

Example 2

Figure 3:
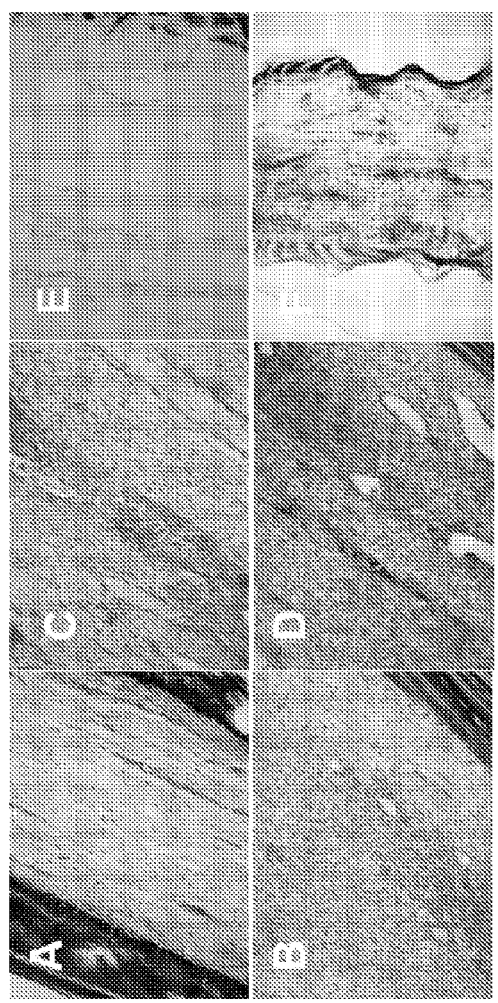
FIG. 3A-F is a set of photomicrographs depicting the recall response in feather tips to *Mycobacterium butyricum*-sensitized chickens.
Figure 3:
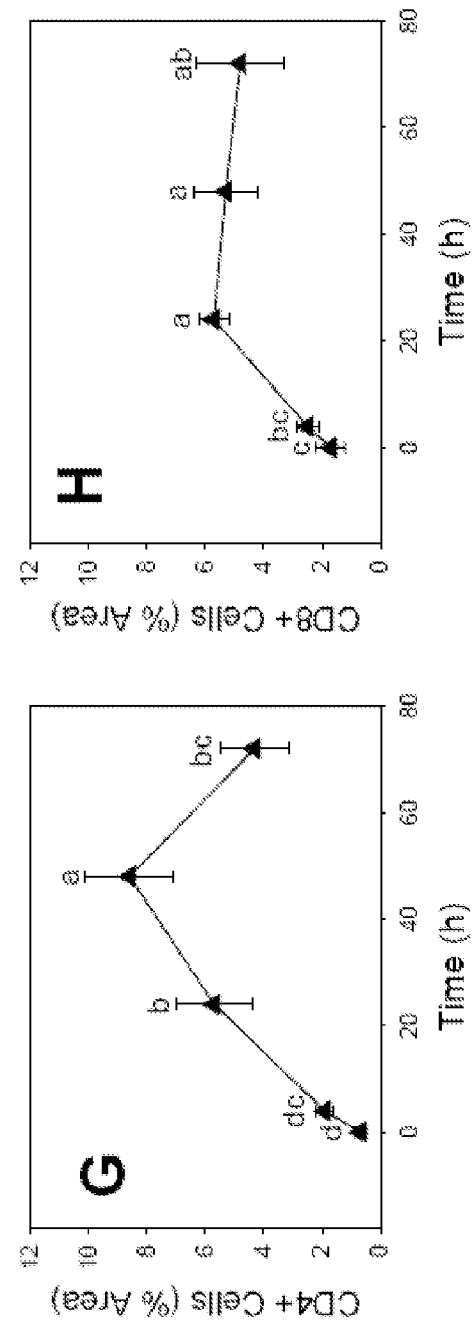
Figure 3:
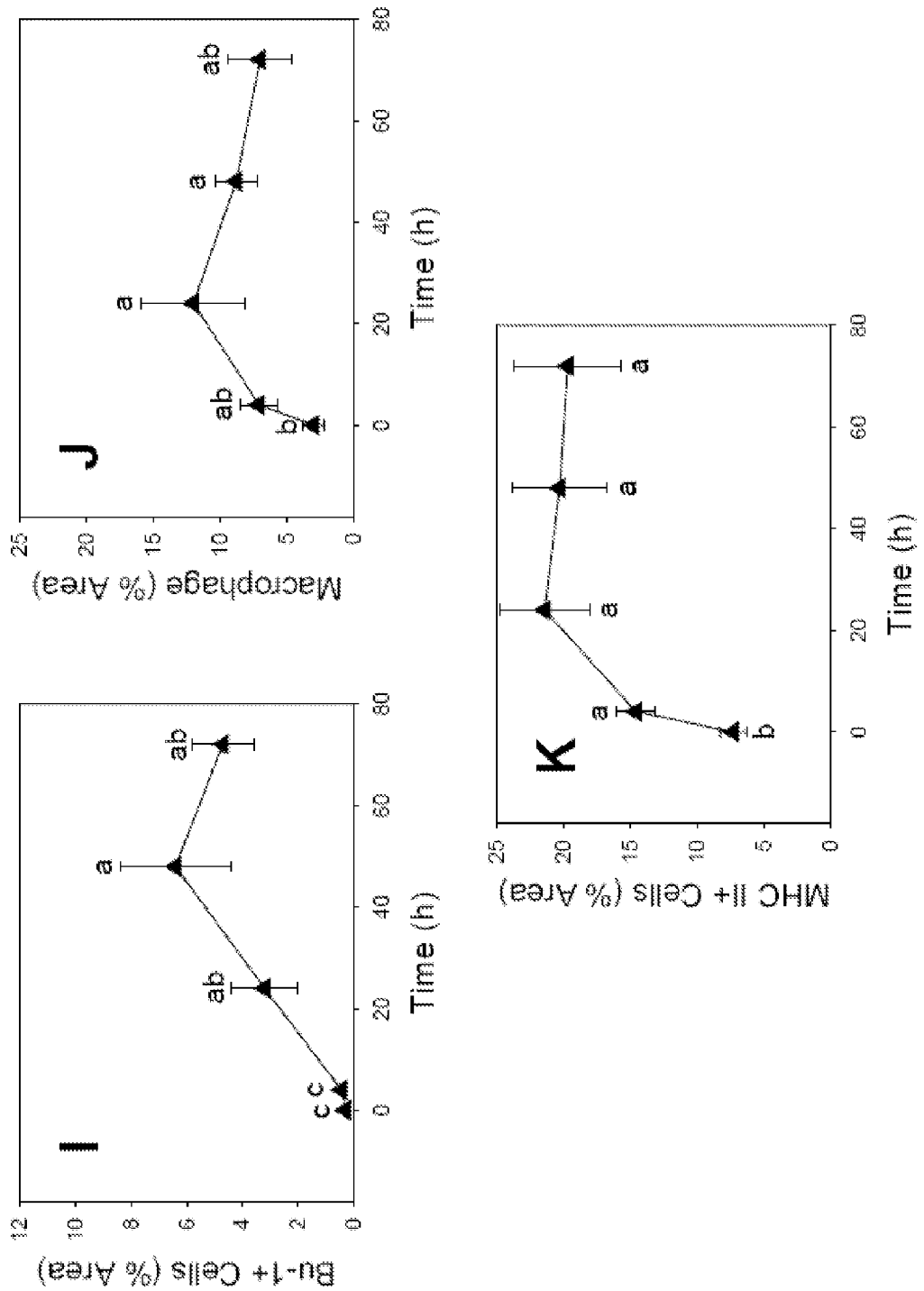

Examination of the in Situ Recall Response to Mycobacterium butyricum (M.b.) in M.b.-Sensitized Individuals We have previously examined the recall response to M.b. in M.b.-sensitized young adult female egg-type chickens over a 72 h period (Ramachandran, I. R., and G. F. Erf 2005. Cell-mediated immunity in chickens: time-course study on lymphocyte infiltration profiles during the wattle response in Ag-sensitized chickens. Poult. Sci. 84 (Suppl. 1):29). That study was the only recall immune response study of poultry that identified the mononuclear cell populations responding to the recall response. Hence, to study the recall response in wing webs and feathers, we decided to use the same antigen (M.b.) and approach. Briefly, 16-wk-old male egg-type chickens were sensitized to M.b. 4 weeks prior to injecting feathers or wing webs with 10 µL or 100 µL of M. b. (0.2 mg/mL) or PBS (vehicle), respectively. At 4, 24, 48 and 72 h post-injection (p.i.), tissues were collected from 8 birds/treatment/time point and processed as described for the LPS/PHA study. PBS injection did not cause leukocyte infiltration in either the feathers or the wing webs, and the feather was much easier to work with than the wing web. M.b. injection resulted in leukocyte infiltration including primarily heterophils at 4 h, a mixture of heterophils and mononuclear cells at the 24 h, and predominantly mononuclear cells at 48 h and 72 h post M.b. injection in both tissues (FIG. 3 A-D—feather). Although lymphocytes and macrophages were observed at 4 h, they were found primarily in perivascular regions. By 24 h lymphocyte aggregates were noted, which increased in size with time (FIG. 3 F). CD4+ lymphocytes were the first T cell to arrive in the tissue, reached peak numbers (% area) at 48 h, and declined at 72 h (FIG. 3G). The number of CD8+ lymphocytes increased for the first 24 h, and then remained at that level at 48 and 72 h (FIG. 3H). Bu-1+ cells (B cells) also infiltrated the feather, with similarly high numbers present at 24 through 72 h (FIG. 3I). The number of KUL01+ cells (monocytes/macrophages) increased sharply over the first 48 h and remained at that level through the 72 h. Mononuclear cell infiltration was associated with substantial increase in MHC class II positive cells, including macrophages, lymphocytes and endothelial cells. This indicates that infiltrating cells, especially T cells, were activated and suggests the local production of IFN-γ. These results were almost identical to those observed in the wattle study and appear to be similar to events occurring in the wing web.

Example 3

Recall Response to Components of a Vaccine for Avian Influenza (AI) Virus

To investigate whether a candidate avian influenza vaccine is capable of eliciting a recall response, the feather injection method was used. The vaccine included M2e, a protein that is common to AI viruses but that is not very immunogenic. To enhance immune recognition and to reduce cost and effort needed to administer the vaccination, an attenuated ΔaroA *Salmonella entertitidis* strain (ΔSE) that expresses the epitope M2e, with or without 10 aa sequence of CD154 (CD40 ligand) was used as a carrier. The vaccine is orally administered. Based on antibody production, the results were very favorable demonstrating a good humoral response to M2e. To examine cell-mediated immune activity initiated to the various vaccine preparations, we conducted a recall response study using the feather injection method. Feathers of the same individual were injected with different components of the recall antigen. The study indicated low cell-mediated recall immune activity to M2e, very low activity to primary injection of BSA, no activity to PBS injection, and substantial cellular activity, primarily inflammatory activity, to Salmonella (Higgins, S. E., S. L. Layton, A. D. Wolfenden, K. Cole, B. M. Hargis, and G. F. Erf. 2007. In vivo characterization of the recall response to antigen in chickens vaccinated with attenuated *Salmonella* mutants expressing M2e protein. Poult. Sci. 86 (Suppl. 1):53). Multiple recall antigen injection into different feathers will be a highly valuable application of the feather method.

Example 4

Local Tissue Response to Injection of Interferon-Gamma (IFN-γ)

To investigate the local tissue effect of interferon gamma (IFN-γ), 5 growing feathers on each breast tract of eight 10-week old female egg-type chickens were injected with 10 μL of 10 ng/mL of recombinant chicken IFN-γ. Feathers of age-matched controls (7) were injected with PBS. Feathers were collected at 6 h, 1 day (24 h), 2- and 3 days-post-injection, one for histological analysis and 1 for gene-expression analysis. Preliminary histological analysis revealed mononuclear cell infiltration into the feather pulp, but no granulocytes, by 6 h. The infiltration continued to increase by 24 h and remained elevated at 2 and 3 days post-injection. Based on visual scoring of the extent of mononuclear infiltration (score 1=no infiltration, 5=extensive infiltration throughout the entire pulp), the mean score for PBS was 1.1±0.1 and for IFN-γ was 1.6±0.1, 4.0±0.5, 3.2±0.6, and 3.0±0.9 at 6 h-, and 1-, 2-, and 3 days-post-injection, respectively. Quantitative and qualitative analysis (using an image analysis program), immunohistochemical staining, and gene-expression analyses are in progress.

Example 5

Primary and Secondary Responses to Herpesvirus of Turkey (HVT) Vaccine Virus To examine the local tissue response following the injection of HVT (live virus, Marek's disease virus serotype 3, vaccine virus), 16-week-old female egg-type chickens were vaccinated with cell-free HVT at hatch (10 birds; secondary response group) or not vaccinated with cell-free HVT at hatch and kept in isolation (10 birds; primary response group). Feather pulps of growing feathers were injected with 10 μL of cell free HVT vaccine virus (2×5 growing feathers on each breast tract, controls were PBS injected). Two feather tips were collected at 1-, 2-, 3-, and 5-days post-injection, one for histological analysis and 1 for gene-expression analysis. Preliminary histological analysis revealed mononuclear cell infiltration into the feather pulp in both groups (primary and secondary exposure to HVT). Only 2 birds from the primary response group had mixed cell infiltration of heterophils (15%) and mononuclear cells (85%) on day 1. Based on visual scoring of the extent of mononuclear infiltration (score 1=no infiltration, 5=extensive infiltration throughout the entire pulp), the mean score for PBS was 1.11±0.1. For birds from the primary response group, the mean infiltration score was 1.9±0.2, 2.1±0.2, 2.3±0.2 and 1.8±0.3 for day 1, 2, 3, and 5 post-injection, respectively. For birds from the secondary response group, the mean infiltration score was 1.5±0.2, 1.8±0.1, 1.4±0.1 and 1.4±0.1 for day 1, 2, 3, and 5 post-injection, respectively. Quantitative and qualitative analysis (using an image analysis program), immunohistochemical staining, and gene-expression analyses are underway.

Example 6

Future Directions

Immunofluorescent staining and pulp cell population analyses by flow cytometry: Feather pulp will be collected from 4 feathers, pushed through a 60 μm (pore size) nylon mesh, the resulting single cell suspension will be washed twice with PBS+ and the cells evenly distributed into 10 wells for direct three color staining using the following combinations of monoclonal antibodies: Triple Tag isotype control (mix of mouse IgG1 conjugated with FITC (F), PE (P), and biotin (B) used with APC-labeled strepavidin); CD4-F, CD8α-PE, γδTCR (TCR1)-B; CD4-F, CD8α-PE, αβ1TCR (TCR2)-B; CD4-F, CD8α-PE, αβ2TCR (TCR3)-B; CD8β4-F, CD8α-PE, TCR1-B; CD8β4-F, CD8α-PE, TCR2-B; CD8β4-F, CD8α-PE, TCR3-B; CD4-F, Ia-PE, CD44-B; IA-F, CD8α-PE, CD44-B; cIgG-F, Bu-1-PE and cIgM-B. Cell population data will be acquired using a Becton Dickinson FACSort/FACS Calibur flow cytometer (blue and red laser). The proportions of marker-defined cell populations within the pulp cell suspensions will be examined by one-, two-, and three-color analyses using CellQuest. See Shresta, S., J. R. Smyth, Jr., and G. F. Erf. 1997. Profiles of pulp infiltrating lymphocytes at various times throughout feather regeneration in Smyth line chickens with vitiligo. Autoimmunity 25:193-201; Erf, G. F., W. G. Bottje, T. K. Bersi, M. D. Headrick, and C. A. Fritts. 1998. Effects of dietary vitamin E supplementation on the immune system in broilers: Altered proportions of CD4 T cells in thymus and spleen. Poult. Sci. 77:529-537; and Wang, W., G. F. Erf, and R. F. Wideman. 2002. Effect of cage vs. floor litter environments on the pulmonary hypertensive response to intravenous endotoxin and on blood-gas values in broilers. Poult. Sci. 81:1728-1737.

Targeted gene expression analysis by real-time quantitative RT-PCR: To perform qRT-PCR on feather tissue, total RNA will be extracted from RNAlater preserved feathers using the RNAeasy kit (Qiagen Corp). The quality and quantity of RNA will be assessed using the Experion Automated Electrophoresis System (Bio-Rad Laboratories). Isolated RNA will be stored at −80° C. until use. qRT-PCR will be performed using relevant primers, species-specific TaqMan probes and TaqMan and one-step RT-PCR Master Mix. Targets to be examined include the chicken orthologues of iNOS, type I interferons (IFN-α & β), pro-inflammatory (IL-1β, IL-6, CXCLi2 (IL-8)), Th1 (IL-2, IL-12α and β, IL18 and IFN-γ) and Th2 cytokines (IL-4, TGF-β4), chemokines CXCLi1 and CCLi4, and viruses (HVT and ARV). Primers and probes will be designed as described. Primers and probes for the chicken orthologues of HSP 70, Ig-λ, and granzyme A will be designed using the relevant gene sequences obtained from the chicken genomic database published in GenBank (accession number NM 001006685, XM 001232583, NM 204457, respectively). Primers and probes will be designed using Primer Express® software 3.0 (Applied Biosystem). Probes will be designed to target exonic sequences that flank a large intron to minimize detection of contaminating DNA. Probes will be labeled with the fluorescent reporter dye 5-carboxyfluorescein (FAM) at the 5' end and the quencher N,N,N,N'-teramethyl-6-carboxyrhodamine (TAMRA) at the 3' end. The assays will be performed on an ABI PRISM 7300 Sequence Detection System (Applied Biosystems). The cycling parameters for reverse transcription and PCR will be followed as recommended in the commercial kits used. Primers and probes for 28S will be included as an endogenous control in this study to normalize the data for quantitative comparison. Other controls such as no template controls as well as RNA isolated from cells/tissues known to produce/not produce these mediators will be included. Depending on indices obtained from other assessments more (e.g., integrins, pro- and anti-apoptotic factors) or fewer targets will be examined using this method.

The quantification of relative gene expression will be carried out by using the comparative $C_T$ method, which is also known as the $\Delta\Delta C_T$ (delta delta $C_T$) method. For each target, a validation experiment will be carried out as described in Applied Biosystem's User Bulletin #2 before using the $\Delta\Delta C_T$ method to quantify relative gene expression. Relative gene expression of the targets will be calculated as follows: 1) $\Delta C_T = C_T$ target-$C_T$ reference (endogenous control); 2) $\Delta\Delta C_T = \Delta C_T$ test sample-$\Delta C_T$ calibrator sample. The fold change in gene expression relative to the calibrator sample (0 h) will be computed as: Fold change=$2^{-\Delta\Delta C_T}$.

I claim:

1. A method of evaluating a tissue response to an agent comprising; a) administering the agent to a bird; b) injecting the agent or a portion thereof into a first feather tip of the bird at a time after step (a); and c) evaluating the tissue response to the agent in the first feather tip.

2. The method of claim 1, wherein the agent is administered by injection into the first feather tip in step (a).

3. The method of claim 1, wherein the agent is selected from the group consisting of polypeptides, polynucleotides, carbohydrates, lipids, microbes, cells, pharmaceuticals and portions or combinations thereof.

4. The method of claim 1, wherein the tissue response is evaluated by histological analysis of the first feather tip.

5. The method of claim 1, wherein evaluating the tissue response comprises harvesting cells from the first feather tip.

6. The method of claim 5, wherein the cells are cultured in vitro.

7. The method of claim 5, wherein the cells are analyzed by FACS.

8. The method of claim 1, wherein the tissue response is evaluated by assessing enzyme activity in cells in the first feather tip.

9. The method of claim 1, wherein the tissue response is evaluated by assessing protein production in cells in the first feather tip.

10. The method of claim 1, wherein the tissue response is evaluated by assessing nucleic acid expression in the first feather tip.

11. The method of claim 1, wherein the tissue response to the agent in the bird is evaluated over time.

12. The method of claim 11, further comprising injecting the agent or a portion thereof into a second feather tip of the bird, harvesting the second feather tip from the bird at a time different than when the first feather tip was harvested and evaluating the tissue response in the second feather tip.

13. The method of claim 12, wherein the first feather tip and second feather tip are injected at different times.

14. The method of claim 12, wherein the first feather tip and the second feather tip are injected substantially simultaneously.

15. The method of claim 1, wherein the bird is selected from the group consisting of a turkey, a chicken, a quail, an emu, a bluejay, a crow and a duck.

16. The method of claim 1, wherein the agent is a vaccine or a portion thereof.

17. The method of claim 16, wherein the development of a tissue response in the feather tip is indicative of a vaccine specific immune response.

18. A method of monitoring exposure to an agent comprising: a) injecting a first feather tip of a bird with the agent; and b) monitoring the tissue response to the agent in the first feather tip, wherein the development of a tissue response in the first feather tip is indicative of exposure to the agent.

19. A method of evaluating a tissue response to an agent comprising: a) administering the agent to a first feather tip of a bird by injection; and b) evaluating the tissue response to the agent in the first feather tip.

20. A method of evaluating an effect of an agent on the tissue response of a bird comprising: a) administering the agent to the bird; b) injecting an antigen into a first feather tip of the bird; and c) evaluating the tissue response to the antigen after exposure to the agent.

* * * * *